United States Patent
Zipplies et al.

(10) Patent No.: US 8,440,858 B2
(45) Date of Patent: May 14, 2013

(54) METHOD OF MAKING FLUORINATED ALKOXY CARBOXYLIC ACIDS AND PRECURSORS THEREOF

(75) Inventors: Tilman Zipplies, Burghausen (DE); Klaus Hintzer, Kastl (DE); Oleg Shyshkov, Burgkirchen (DE)

(73) Assignee: 3M Innovative Properties Company, Saint Paul, MN (US)

( * ) Notice: Subject to any disclaimer, the term of this patent is extended or adjusted under 35 U.S.C. 154(b) by 2 days.

(21) Appl. No.: 13/133,734

(22) PCT Filed: Nov. 24, 2009

(86) PCT No.: PCT/US2009/065677
§ 371 (c)(1),
(2), (4) Date: Jun. 9, 2011

(87) PCT Pub. No.: WO2010/071730
PCT Pub. Date: Jun. 24, 2010

(65) Prior Publication Data
US 2011/0245520 A1    Oct. 6, 2011

(30) Foreign Application Priority Data
Dec. 19, 2008  (GB) .................................. 0823120.1

(51) Int. Cl.
*C07C 51/08*  (2006.01)

(52) U.S. Cl.
USPC ......................................................... 562/586

(58) Field of Classification Search ................... 562/586
See application file for complete search history.

(56) References Cited

U.S. PATENT DOCUMENTS
2006/0281946 A1  12/2006  Morita et al.
2007/0025902 A1  2/2007  Hintzer et al.

FOREIGN PATENT DOCUMENTS
EP      1 170 275         1/2002
WO     WO 2007/030314     3/2007

OTHER PUBLICATIONS

Arthur et al., "Addition of Hydrogen Cyanide to Unsaturated Compounds," *J. Am. Chem. Soc.*, 1954, 76, 5364-5367.
Baker et al., "Chiral Aryl Diphosphites: a New Class of Ligands for Hydrocyanation Catalysis," *J. Chem. Soc. Chem. Commun.*, 1991, 1292-1293.
Furin et al., "Reaction of 1,1,2-trifluoro-2-hexafluoro-2'-(heptafluoropropoxy)-propoxyethylene with amines or alcohols," *Journal of Fluorine Chemistry*, 106 (2000) 13-24.
Goertz et al., "Application of chelating diphosphine ligands in the nickel-catalysed hydrocyanation of alk-l-enes and ω-unsaturated fatty acid esters," *Chem. Commun.*, 1997, 1521-1522.
Gubanov V. et al., "Reaction of perfluoromethyl perfluorovinyl ether with hydrogen halides," *Zhurnal Obshchei Khimii, Nauka*, Moscow, RU, vol. 34, No. 8, Jan. 1, 1964, 2802-2803.
RajanBabu, et al., "Electronic effects in asymmetric catalysis: enantioselective carbon-carbon bond forming processes," *Pure & Appl. Chem.*, vol. 66, No. 7, 1994, 1535-1542.
Weissermel et al., *Industrial Organic Chemistry*, Wiley-VCH Verlag 2003, ISBN 3-527-30578-5, p. 249.
Yan et al., "Asymmetric hydrocyanation of olefins catalyzed by chiral diphosphite-nickel complexes," *Tetrahedron: Asymmetry*, 11 (2000) 845-849.

*Primary Examiner* — Kristin Bianchi
(74) *Attorney, Agent, or Firm* — C. Michael Geise

(57) ABSTRACT

A method for preparing saturated partially fluorinated alkoxy carboxylic acids or salts thereof by treating a compound: (II), where $R_f$ represents a fluorinated, linear or branched alkyl residue interruptible by one or more oxygen atoms, n is 0 or 1, with a Z-anion in a reaction medium comprising water and an organic solvent, where the Z-anion is selected from CN—, SCN— and OCN— or combinations thereof. A method of making partially fluorinated ethers of the general formula (I) wherein $R_f$ is defined as above, n is 0 or 1, and Z is nitrile (—CN), azide (—$N_3$), thiocyanate (—SCN) or cyanate (—OCN) group, said method comprising treating a fluorinated olefin of the general formula (II) wherein the Z-anion is CN—, OCN—, SCN— or $N_{3-}$. A compound of the general formula (I) as previously described where Z is selected from SCN, OCN and $N_3$.

5 Claims, No Drawings

METHOD OF MAKING FLUORINATED ALKOXY CARBOXYLIC ACIDS AND PRECURSORS THEREOF

CROSS REFERENCE TO RELATED APPLICATIONS

This application is a national stage filing under 35 U.S.C. 371 of PCT/US2009/065677, filed Nov. 24, 2009, which claims priority to Great Britain Application No. 0823120.1, filed Dec. 19, 2008, the disclosures of which are incorporated by reference in their entirety herein.

FIELD OF THE INVENTION

The invention relates to processes of making partially fluorinated alkoxy carboxylic acids. In another aspect the invention relates to partially fluorinated alkyl ethers containing terminal nitrile (—CN), thiocyanate (—SCN), cyanate (—OCN) or azide (—$N_3$) groups and to methods of making them.

BACKGROUND ART

Fluorinated saturated alkyl and alkoxy ethers containing one or more terminal nitrogen-containing functional groups, in particular those selected from nitriles, thiocyanates, cyanates and azides are useful materials in the fluoropolymer industry.

Fluorinated saturated alkyl and alkoxy ethers containing terminal azides groups can be used as cross linker in the preparation of fluoroelastomers. Therefore, there is a need to provide simple and effective methods to provide saturated fluorinated alkyl or alkoxy ethers containing terminal azide groups.

Fluorinated alkyl and alkoxy ethers containing terminal cyanates, thiocyanate and, in particular, nitrile groups can be converted into terminal carboxylic acids by hydrolysis of the nitrile, cyanate or thiocyanate groups. Partially fluorinated alkoxy carboxylic aids have been proposed as alternative and more environmentally-friendly (more biodegradable) emulsifiers replacements for perfluorooctanoic acid ($CF_3(CF_2)_6$COOH) and its salts, which have been commonly used as emulsifiers in the preparation of fluoropolymers by aqueous emulsion polymerization. Various methods for the preparation of partially fluorinated alkoxy carboxylic acids have been described, which, however, involve complex and cumbersome processes. For example, U.S. Pat Appl. No. 2006/0281946, to Morita et al, describes partially fluorinated carboxylic acid emulsifiers of the general formula Rf1(OCH$_2$CF$_2$CF$_2$)$_{n1}$OCX$_1$X$_2$CF$_2$(Rf2)$_{n2}$COOM where Rf1 represents a straight or branched fluoroalkyl group containing 1 to 20 carbon atoms, Rf2 represents a straight or branched fluoroalkylene group containing 1 to 25 carbon atoms, n1 represents an integer of 0 to 3, n2 represents an integer of 0 or 1, $X_1$ and $X_2$ are the same or different and each represent H or F and M represents $NH_4$ or a monovalent metal element. These acids were reported to be obtainable by a ring opening addition of tetrafluorooxetane to a fluorine-containing acid fluoride followed by the conversion of the acid fluoride to the carboxylic acid. Such reaction sequence involves various reaction steps and is therefore technically difficult costly. In another publication (U.S. Pat. Appl. No 2007/0025902 to Hintzer et al), several fluorinated alkoxy carboxylic acid emulsifiers and several methods of their preparation are described. For example, fluorinated carboxylic acids of the general formula Rfa-(O)$_t$—CHF—(CF$_2$)—COOH, wherein Rfa represents a linear fully or partially fluorinated aliphatic group optionally interrupted by one or more oxygen atoms and t represents 1 or 0 were described to be obtainable by a free radical reaction of a fluorinated olefin of the formula Rfa-(O)$_t$—CF=CF$_2$ with methanol followed by oxidation of the reaction product using a suitable oxidizing agent. For the oxidation metal oxides, such as $KMnO_4$, $RuO_4$, $OsO_4$ or chromium (VI) oxide were suggested. Preparing the carboxylic acids in an industrial scale using such agents leads to cost-intensive waste treatment for removing residues the oxidizing agents. Although the above described methods may be used to prepare partially fluorinated alkoxy carboxylic acids, the need exists for alternative methods, in particular for the large scale production of the acids. Desirably, such methods allow the preparation of such acids in a simple and/or cost-effective process.

SUMMARY

It has been found that partially fluorinated alkyl ethers of the general formula

wherein $R_f$ represents a fluorinated, linear or branched alkyl residue which may be interrupted by one or more oxygen atoms, n represents either 0 or 1, and Z represents nitrile (—CN), azide (—$N_3$), thiocyanate (—SCN) or cyanate (—OCN) group, may be prepared in a one-step reaction.

Ethers according to general formula (I) may be isolated or used as intermediates and may be directly converted into the corresponding carboxylic acid by hydrolysis.

Therefore, in the following there is provided a method of making partially fluorinated ethers of the general formula

wherein $R_f$ represents a fluorinated, linear or branched, alkyl residue which may be interrupted by one or more oxygen atoms, n represents either 0 or 1, and Z represents nitrile (—CN), azide (—$N_3$), thiocyanate (—SCN) or cyanate (—OCN), said process comprising treating a fluorinated olefin of the general formula

wherein $R_f$ and n are defined as above, with a Z-anion, wherein the Z-anion is selected from $CN^-$, $OCN^-$, $SCN^-$ or $N_3^-$.

In cases where Z is a nitrile, cyanate or thiocyanate group, the ethers according to formula (I) may hydrolyse into carboxylic acids in the presence of water. Therefore there is also provided a process for preparing saturated partially fluorinated alkyl or alkoxy carboxylic acids or salts thereof, said process comprises treating a fluorinated olefin of the general formula

wherein $R_f$ and n are defined as above, with a Z-anion in a reaction medium comprising water and an organic solvent, wherein the Z-anion is selected from $CN^-$, $SCN^-$ and $OCN^-$ or combinations thereof.

In a further aspect there is provided a method for preparing partially fluorinated saturated carboxylic acids of the general formula

wherein Rf and n are defined as above and wherein M⁺ represents a monovalent cation, method comprising said treating a fluorinated olefin of the general formula $$R_f\text{—}O\text{—}(CF_2)_n\text{—}CF\text{=}CF_2 \qquad (II),$$

wherein $R_f$ and n are defined as above, with a CN⁻ anion in a reaction medium comprising water and an organic solvent.

In yet another aspect there is provided a compound of the general formula $$R_f\text{—}O\text{—}(CF_2)_n\text{—}CHF\text{—}CF_2\text{—}Z \qquad (I),$$

wherein n and $R_f$ are defined as above and wherein Z is selected from SCN, OCN and $N_3$.

DETAILED DESCRIPTION

Before any embodiments of this disclosure are explained in detail, it is to be understood that the disclosure is not limited in its application to the details of construction and the arrangement of components set forth in the following description. The invention is capable of other embodiments and of being practiced or of being carried out in various ways. Also, it is to be understood that the phraseology and terminology used herein is for the purpose of description and should not be regarded as limiting. Contrary to the use of "consisting", the use of "including," "comprising," or "having" and variations thereof herein is meant to encompass the items listed thereafter and equivalents thereof as well as additional items. The use of "a" or "an" is meant to encompass "one or more". Any numerical range recited herein includes all values from the lower value to the upper value. For example, if a concentration range is stated as 1% to 50%, it is intended that values such as 2% to 40%, 10% to 30%, or 1.5% to 3.9%, etc., are expressly enumerated. These are only examples of what is specifically intended, and all possible combinations of numerical values between and including the lowest value and the highest value enumerated are to be considered to be expressly stated in this application.

As used herein the term "fluorinated" means the compound contains one or more F atoms.

The term "partially fluorinated" means the compounds contains at least one —CHF— group and/or one or more of the following combinations:
at least one —CF₂— and/or at least one —CF₃ group and one or more of the following groups: —CH₂—, —CH₃, =CH₂, and/or =CH— groups.

As used herein the term "fully fluorinated" or "perfluorinated" means the compound or residue can be derived from a hydrocarbon and all hydrogen atoms have been replaced by F atoms. For example, a perfluorinated compound may contain —CF₃ and/or —CF₂— groups but no —CHF, —CH₂, =CH—, =CH₂ or —CH₃ groups. A perfluorinated compound may contain catenary heteroatoms selected from oxygen, nitrogen or sulphur atoms, such as for example, but not limited to CF₃—O— or CF₃—CF₂—O— and the like. Preferably, the perfluorinated compound or residue contains no catenary heteroatoms or only oxygen catenary heteroatoms.

The processes provided herein make accessible a wide range of functionalized saturated fluorinated ethers by reaction of Z-containing anions (wherein Z-containing anions are CN⁻, SCN⁻, OCN⁻ and $N_3^-$) with fluorinated alkoxy olefins of the general formula $$R_f\text{—}O\text{—}(CF_2)_n\text{—}CF\text{=}CF_2 \qquad (II).$$

Although, the vinyl and allyl ethers of formula (II) contain in proximity to their olefinic moiety an Rf—O residue which can be expected to be easily cleaved off as alcoholate (Rf—O⁻) upon nucleophilic attack and may then further decompose, it was found that such cleavage can be avoided or suppressed when the comparatively small Z-anions (CN⁻, SCN⁻, OCN⁻ and $N_3^-$) are used as nucleophiles.

Z-anion sources, such as ammonium or metal salts containing a Z-anion and corresponding proton acids are typically water soluble, while the fluorinated alkoxy ethers typically are not. Furthermore, a proton source, which delivers protons (H⁺) is required to complete the reaction to give compounds of general structure (I)

$$R_f\text{—}O\text{—}(CF_2)_n\text{—}CFH\text{—}CF_2\text{—}Z \qquad (I)$$

wherein $R_f$ represents a fluorinated, linear or branched, alkyl residue which may be interrupted by one or more oxygen atoms, n represents either 0 or 1, and Z represents a nitrile (—CN), azide (—$N_3$), thiocyanate (—SCN) or cyanate (—OCN) group.

Surprisingly good yields of the desired reaction products can be obtained if the reaction is carried out in the presence of water, which can be used to dissolve the anion source while in the same time serving as a proton source. Z-containing anions, in particular cyanides, are readily available and are widely used as reaction materials in the chemical industry (for example in the preparation of methacrylic acid etc. and plastics prepared therefrom). Established and cost-effective waste treatment procedures are in place.

Furthermore, fluorinated ethers according to formula (I) containing nitrile-, cyanate- and thiocyanate-groups in terminal positions can be oxidized to carboxylic acids by hydrolysis in the presence of water in a one-step reaction starting from the ethers according to formula (II). The conversion does not require strong oxidizing agents, such as for example metal peroxides and the like.

The processes provided herein allow using readily available water soluble materials providing CN⁻, SCN⁻, OCN⁻ and $N_3^-$ anions to make addition products and/or carboxylic acids. Many fluorinated olefinic vinyl and allyl ethers are also commercially available avoiding the costly synthesis of starting materials or intermediates.

The reactions can be carried out in a one-step reaction starting from the ether according to formula (II). The reactions may be carried out to give good yields (for example yields greater than 30%, or greater than 50% or even greater than 70% may be obtained).

Fluorinated Olefinic Ethers

Fluorinated olefinic ethers are used as starting materials in the processes provided herein. Suitable fluorinated ethers correspond to the general formula $$R_f\text{—}O\text{—}(CF_2)_n\text{—}CF\text{=}CF_2 \qquad (II),$$

wherein n is either 1, in which case formula (II) represents an allyl ether, or n is 0, in which case formula (II) represents a vinyl ether.

$R_f$ represents a fluorinated or a perfluorinated, linear or branched aliphatic residue which may be interrupted by one or more oxygen atoms.

Rf may contain from 1 to 10 carbon atoms and may contain 0, 1, 2 or 3 catenary oxygen atoms.

In one embodiment Rf corresponds to Rf1' wherein Rf1' has the general formula $$Rf1\text{-}[ORf2]_p\text{-}[ORf3]_q\text{-} \qquad (Rf1')$$

in which Rf1 is a linear, cyclic or branched, partially or fully fluorinated aliphatic group of 1 to 10 carbon atoms, (for example 1, 2 or 3, preferably —CF₃), Rf2 and Rf3 each independently represent a linear perfluorinated alkylene of 1, 2, 3 or 4 carbon atoms and p and q each independently represent 1, 2, 3 or 4, wherein the total number of carbon atoms in Rf1' is equal to or less than 10.

In another embodiment Rf corresponds to Rf2' wherein Rf2' has the general formula

Rf4-O—(CF$_2$)$_b$—   (Rf2')

in which Rf4 is a linear, cyclic or branched, partially or fully fluorinated alkylene having 1, 2, 3 or 4 carbon atoms, preferably —CF$_3$, and b represents 1, 2, 3, 4, 5 or 6 and wherein the total number of carbon atoms in Rf2' is equal to or less than 10.

In yet another embodiment Rf corresponds to Rf3' which has the formula

Rf5-(CF$_2$)$_c$-   (Rf3')

in which Rf5 is a linear, cyclic or branched, partially or fully fluorinated alkylene having 1, 2, 3 or 4 or up to 9 carbon atoms, preferably —CF$_3$, —O—CF$_3$, —CF—CF$_3$ of O—CF$_2$—CF$_3$ and c represents 1, 2, 3, 4, 5 or 6 and wherein the total number of carbon atoms in Rf3' is equal to or less than 10. In some embodiments Rf5 is —CF$_3$, —O—CF$_3$, —CF—CF$_3$ of O—CF$_2$—CF$_3$ and c is 1, 2, 3, 4 or 5.

In a further embodiment Rf corresponds to Rf4' which has the formula

Rf6-O—(CF$_2$)$_d$—O—(CF$_2$)$_e$—   (Rf4')

in which Rf6 is a linear, cyclic or branched, partially or fully fluorinated alkylene having 1, 2, 3 or 4 carbon atoms, preferably —CF$_3$, and d and e each independently represent 1, 2, 3 or 4 and wherein the total number of carbon atoms in Rf4' is equal to or less than 10.

In one embodiment, residues Rf1, Rf4, Rf5 and Rf6 of the above embodiments are linear. In another embodiment, residues Rf1, Rf4, Rf5 and Rf6 are linear and perfluorinated, preferably and only containing 0 or 1 catenary heteroatom, wherein the heteroatom is selected from oxygen.

The fluorinated olefinic alkyl ethers may be introduced into the reaction as liquids or dissolved or dispersed in a solvent, or in gaseous form. The reaction can be carried out at pressures greater than ambient pressure, for example if the ethers are used in gaseous form or when it is desired to keep the ethers in their liquid form. Typically, the reaction is carried out at a pressure of 1 bar to up to 20 bar, preferably at a pressure about ambient pressure.

Z-Anions and Sources Thereof

In the processes provided herein the olefins of formula (II) are treated with Z-anions (also referred to herein as Z$^-$). Z-anions (Z$^-$) as used herein include CN$^-$, OCN$^-$, SCN$^-$, N$_3^-$.

The Z-anions may be provided by a suitable Z-anion containing source. Suitable anion sources include metal salts, ammonium salts, alkylammonium salts and the like. Suitable Z-anion containing sources also include the corresponding proton acids, including, for example, HCN, HOCN, HSCN and HN$_3$.

Preferably, the Z-anion containing sources are water soluble. Typically, a salt is considered water soluble if at least 0.1 mol, preferably at least 1.0 mol of the salt dissolves in 1 L of distilled water at ambient conditions (25° C., 1 bar).

Suitable salts include but are not limited to salts of the type M$^+$Z$^-$, M$^{2+}$(Z$^-$)$_2$ or proton acids of the type H$^+$Z$^-$, wherein Z$^-$ represents CN$^-$, OCN$^-$, SCN$^-$ or N$_3^-$, M$^+$ represents a monovalent metal cation, including, for example Na$^+$, K$^+$, Li$^+$ or an ammonium (NH$_4^+$) or alkylammonium cation and the like, M$^{2+}$ represents a divalent metal cation including, for example, Ca$^{2+}$, Mg$^{2+}$ and the like, most preferably the salts are water-soluble.

Conversion to Partially Fluorinated Ethers Containing One or More Terminal Z-Groups The above-described olefinic ethers can be subjected to treatment with nitrogen-containing anions of the general formula Z$^-$ in the presence of a proton source form a partially fluorinated saturated ether of the general formula

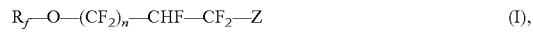

R$_f$—O—(CF$_2$)$_n$—CHF—CF$_2$—Z   (I), with n representing 0 or 1 and Z and R$_f$ being defined as above, including the embodiments where R$_f$ has a structure according to Rf1'-Rf4' as described above.

The proton (H$^+$) source can be water, or it may be the proton of a proton acid HZ. The reaction is typically carried out in a solvent containing water to provide a source for H$^+$. However, it is contemplated that the reaction can also be carried out in the absence of water, in which case the H$^+$ may be provided from another source, for example, by providing the nitrogen-containing anions (Z$^-$) in the form of their proton acids (HZ). In this case catalysts may be used.

When water is used as solvent to carry out the reaction, either a phase transfer catalyst is used or the water is present as co-solvent, meaning it is present in a mixture with at least one organic solvent. Preferably a mixture of water and one or more organic solvents is used to perform the reaction. The organic solvent may or may not be miscible with water and the reaction can be carried out as a one-phase or two-phase reaction. The organic solvent is preferably capable of at least partially dissolving the fluorinated olefinic ether. Preferably the organic solvent is capable of at least partially dissolving the Z$^-$ source. Preferably, the organic solvent is capable of dissolving at least 0.1 mol of the Z$^-$-source at ambient conditions (25° C., 1 bar) in 1 L of solvent.

The organic solvent is preferably polar. Polar solvents include hydrocarbons that are liquid at room temperature and contain at least one oxygen or nitrogen atom. Moreover, the organic solvent should be inert, which means it does not react as competing nucleophile with the fluorinated olefinic ethers and it does not react with the Z$^-$ anion. Suitable solvents include but are not limited to acetonitrile (CH$_3$CN), dimethylsulfoxide (DMSO), dimethylformamide (DMF), linear, cyclic or branched mono or polyethers derivable from ethylene glycol (HO—CH$_2$CH$_2$—OH) or derivatives thereof, such as, for example, monoglyme, diglyme and the like, linear, branched or cyclic alkyl ethers, such as for example, diethylether, dimethylether ethylbutylether, tetrahydrofurane, crown ethers and the like.

Typically the solvent mixture is chosen such that the amount of water is at least sufficient to provide the required molar amount of H$^+$. Typically, the solvent mixture contains at least an equal amount (by volume) of organic solvent and water, preferably the organic solvent is used in excess for example a volume ratio of water:organic solvent of from 1:1 to about 1:10, about 1:20 or about 1:100.

The pH of the solvent mixture is kept approximately neutral, typically between pH 5 to 9, preferably at pH 6 to 8 or between about pH 6.5 to 7.5.

If only water and no organic solvent is used to carry out the reaction a phase transfer catalyst will be required to carry out the reaction. The use of a phase transfer catalyst may also be required if the volume of organic solvent in the solvent mixture is less than equal to the volume of water used. Phase transfer catalysts as known in the art may be used.

In addition to, or alternative to water as proton source, proton acids of the Z-anions may be used, such as, for example, HCN, HOCN, HSCN or HN$_3$.

The use of the proton acids for preparing and isolating compounds according to formula (I) wherein Z represents a nitrile, a cyanate or a thiocyanate group is recommended, because such compounds are instable in the presence of water and may hydrolyse to carboxylic acids. When treating the fluorinated olefinic ethers according to formula (II) with the proton acids, water is not required to be present as solvent or proton source. Nevertheless organic solvents and/or catalysts may be used to facilitate the reaction.

The reaction may be carried out at temperatures from 0° C. to about 150° C., or from about 20° C. to about 100° C., such as, for example, between 30° C. and 70° C. or between 40° C. and 60° C. and may be adapted to the solvents and starting materials used.

Preferably the reaction is carried out at a temperature and pressure at which the solvent or at least one of the components of a solvent mixture (like water and organic solvent) is in its liquid form or where the solvent of at least one component of a solvent mixture is refluxed.

The reaction can be carried out at ambient, reduced or increased pressures, but typically is carried out at pressures of about 1 bar up to about 20 bars. For example, increased pressures may be used if the fluorinated olefins are volatile or have a low boiling point to keep the olefins in their liquid form, or if the Z-anion source is a proton acid.

The Z-anion source may be added to the fluorinated olefin continuously or discontinuously, in portions or at once. The Z-anion source may be added in equimolar amounts to the olefin or in excess. Alternatively, the olefin may be added to the Z-anion source, for example to a solution or dispersion of the Z-anion source.

In one embodiment there are provided partially fluorinated saturated ethers of the general formula

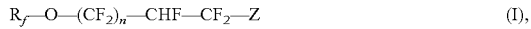

$$R_f-O-(CF_2)_n-CHF-CF_2-Z \quad (I),$$

with n representing 0 or 1 and $R_f$ being as defined as above, including the embodiments where $R_f$ has a structure according to Rf1'-Rf4' as described above and wherein Z is selected from SCN, OCN and $N_3$.

In certain embodiments Rf has a structure according to Rf1' to Rf4' and n is 0, and wherein Rf is preferably linear, more preferably linear and perfluorinated.

In other embodiment Rf has a structure according to Rf1' to Rf4' and n is 1, and wherein preferably Rf is linear more preferably linear and perfluorinated.

Conversion to Partially Fluorinated Alkoxy Carboxylic Acids

The fluorinated alkoxy olefins of formula (II) may be converted into carboxylic acids by treatment with Z-anions via hydrolysis of the intermediary of formula (I) wherein in formula (I) Z represents a nitrile, cyanate or thiocyanate group but wherein Rf and n have the meaning as described above, including the meaning of Rf1' to Rf4'. This reaction can be carried out as a one-step reaction by carrying out the reaction in the presence of water. Water may be used as solvent (in which case a phase transfer catalyst is required or water may be present in a solvent mixture further comprising at least one organic solvent. Preferably a mixture of water and one or more organic solvents is used to perform the reaction. The mixture of water and organic solvent and the process conditions may be used as described above with respect to the conversion to partially fluorinated ethers containing a terminal Z-group.

If only water and no organic solvent is used to carry out the reaction a phase transfer will be required to carry out the reaction. The use of a phase transfer catalyst may also be required if the volume of organic solvent in the solvent mixture is less than equal to the volume of water used.

In addition to, or alternative to water as proton source, proton acids of the Z-anions may be used, such as, for example, HCN, HOCN or HSCN and the reaction product according to formula (I) is prepared and isolated and is then hydrolysed to the acid in a separate step.

The Z-anion source may be added to the fluorinated olefin continuously or discontinuously. The Z-anion source may be added in equimolar amounts to the olefin or in excess. Alternatively, the olefin may be added to the Z-anion source, for example to a solution of dispersion of the Z-anion source.

The carboxylic acid can be isolated from the reaction mixture by converting it into its free acid form, for example by adjusting the pH through addition of acids followed by distillation of the free acid from the reaction mixture. The carboxylic acid may also be isolated by first converting is into an ester (for example by adding an alcohol, preferably methanol or ethanol, preferably in the presence of an acid) and distilling the ester off the reaction the mixture. The collected ester can then be converted into the acid, for example by treating the ester with a base, as known in the art.

In a particular embodiment the processes described herein can be used to prepare fluorinated carboxylic acids of the general formula

$$R_f-O-(CF_2)_n-CFH-CF_2-COO^-M^+ \quad (III).$$

In formula (III) n represents 1 or 0.

M+ represents a cation, in particular a monovalent cation. Monovalent cations include, for example but not limited to, $H^+$ (this case (III) represents the free acid) or a metal cation, including but not limited to $K^+$, $Na^+$ etc and including ammonium or alkylammonium cations, such as $NH_4^+$, tetraalkylammonium and the like, in which case formula (I) represents a carboxylic acid salt.

$R_f$ represents a fluorinated, linear or branched aliphatic residue which may be interrupted by one or more oxygen atoms as described above with respect to compounds according to general formula (I) and including the residues Rf1-Rf4 as described above. Preferably Rf is linear, more preferably linear and perfluorinated.

In this embodiment, ethers of the formula (II) as described above are treated with a $CN^-$— containing salt or with HCN in the presence of a solvent mixture containing water and an organic solvent. The solvent mixtures and reaction conditions with respect to the preparation of carboxylic acids can also be applied here.

Embodiments of the processes described herein will now be further described by way of examples, which are meant to further illustrate the processes described herein but are not meant to be limiting in any way.

It is understood that the processes described herein can also be used to prepare bifunctional terminal compounds of the type

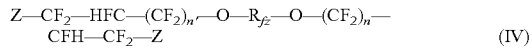

$$Z-CF_2-HFC-(CF_2)_{n'}-O-R_{f2}-O-(CF_2)_n-CFH-CF_2-Z \quad (IV)$$

wherein $R_{f2}$ represents a fluorinated or perfluorinated, linear or branched, alkylene group (preferably containing from 1 to 6 carbon atoms, which may be interrupted by one or more oxygen atoms, n and n' represent independently from each other 0 or 1, and Z represents a nitrile (—CN), azide (—$N_3$), thiocyanate (—SCN) or cyanate (—OCN) group, said method comprising treating a fluorinated olefin of the general formula

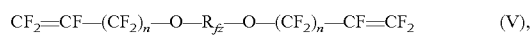

$$CF_2=CF-(CF_2)_{n'}-O-R_{f2}-O-(CF_2)_n-CF=CF_2 \quad (V),$$

wherein $R_f$, n' and n are defined as above, with a Z-anion, wherein the Z-anion is selected from $CN^-$, $OCN^-$, $SCN^-$ or $N_3^-$ at the conditions as described above.

Accordingly also bifunctional carboxylic acids can be prepared by hydrolysing compound (IV) in case Z is OOCN, SCN or CN under the conditions as described above. In particular bifunctional carboxylic acid according to (IV) wherein Z represents a carboxylic acid group can be prepared, when a bisolefin according to (V) is reacted with a cyanide ion in a reaction medium containing water and organic solvent in the same way as described above.

EXAMPLES

Example 1

A mixture consisting of 120 ml $H_2O$, 250 ml ethyleneglycol dimethylether and 26.3 g KCN was heated to 50° C. 110 g MV31 ($CF_2$=CF—O—($CF_2$)$_3$—O—$CF_3$) were added to the mixture over a period of 35 min. During the addition of MV31 the temperature of the reaction mixture rose to 57° C. The reaction mixture was cooled down to 25° C. before 55 ml concentrated $H_2SO_4$ were added. The bottom phase was collected and washed with water. Afterwards, the organic phase was mixed with the same volume of conc. $H_2SO_4$ and agitated for 1 h at room temperature. Distillation from the reaction mixture yielded HOOC—$CF_2$—CHF—O—($CF_2$)$_3$—O—$CF_3$ (overall yield 89%).

Example 2

A mixture consisting of 360 ml $H_2O$, 650 ml ethylene glycol dimethylether and 78 g KCN was heated up to 50° C. 440 g MV 31 were added over a period of 60 min. The reaction mixture was further agitated at about 50° C. for 1.5 h. The reaction mixture was cooled to room temperature and acidified with 460 ml of conc. $H_2SO_4$ and 600 ml $H_2O$. The bottom phase was washed with 500 ml conc. $H_2SO_4$. GC- and NMR-measurements revealed an overall conversion of MV31 to $CF_3$—O—($CF_2$)$_3$—O—CHF—$CF_2$—COO$^-$ of 71%.

Example 3

120 ml $H_2O$, 250 ml $CH_3CN$ and 26 g KCN were reacted with 147 g MV 31 at 45° C. as described in Example 2. $CH_3CN$ was distilled off under continuous addition of water. 100 g conc. $H_2SO_4$ and 130 g $CH_3OH$ were added to the solution and the mixture was refluxed for 3 h. The overall yield for the methyl ester was 80%.

Example 4

Comparative 370 g $H_2O$, 26 g KCN and 147 g MV 31 were heated to 50° C. under vigorous agitation. After 24 h, the reaction mixture still showed 2 phases. The conversion of MV 31 was less than 2%; the ratio for $CF_3$—O—$CF_2$—$CF_2$—COO$^-$/$CF_3$—O—$CF_2$—$CF_2$—$CF_2$—O—CHF—$CF_2$—COO$^-$ was 2:1 (determined by GC-MS via prior conversion of the acids into their methylesters).

Example 5

A mixture of 100 ml $H_2O$, 200 ml $CH_3CN$ and 13 g $NaN_3$ were heated to 45° C. 56 g MV 31 were added during 30 min at 45° C. The reaction mixture was agitated at 50° C. for another 1.5 h. $^{19}$F-NMR indicated $CF_3$—O—($CF_2$)$_3$—O—CHF—$CF_2N_3$ in >90% yield.

Example 6

100 ml $H_2O$, 200 ml $CH_3CN$, 12 g $NaN_3$ and 62 g MA 31 ($CF_2$=CF—$CF_2$—O—($CF_2$)$_3$—O—$CF_3$) were reacted at 45-50° C. According to $^{19}$F-NMR $CF_3$—O—($CF_2$)$_3$—O—$CF_2$—CFH—$CF_2$—$N_3$ was formed almost quantitatively.

The invention claimed is:

1. A method for preparing saturated partially fluorinated alkoxy carboxylic acids or salts thereof, said method comprises treating a fluorinated olefin of the general formula $$R_f\text{—O—}(CF_2)_n\text{—CF}\!\!=\!\!CF_2 \quad\quad\quad (II),$$

wherein $R_f$ represents a fluorinated, linear or branched, alkyl residue which may be interrupted by one or more oxygen atoms, n represents either 0 or 1, with a Z-anion in a reaction medium comprising water and an organic solvent, wherein the Z-anion is selected from CN$^-$, SCN$^-$ and OCN$^-$ or combinations thereof.

2. A method for preparing partially fluorinated saturated carboxylic acids of the general formula $$R_f\text{—O—}(CF_2)_n\text{—CFH—}CF_2\text{—COO}^-M^+ \quad\quad\quad (III),$$

wherein $R_f$ represents a fluorinated, linear or branched, alkyl residue which may be interrupted by one or more oxygen atoms, n represents either 0 or 1 and wherein $M^+$ represents a monovalent cation, method comprising said treating a fluorinated olefin of the general formula $$R_f\text{—O—}(CF_2)_n\text{—CF}\!\!=\!\!CF_2 \quad\quad\quad (II),$$

wherein $R_f$ represents a fluorinated, linear or branched, alkyl residue which may be interrupted by one or more oxygen atoms, n represents either 0 or 1, with a CN$^-$ anion in a reaction medium comprising water and an organic solvent.

3. The method according to claim 1 wherein Rf is selected from Rf1', Rf4', Rf5' or Rf6' wherein Rf1' corresponds to the general formula $$\text{Rf1-[ORf2]}_p\text{-[ORf3]}_q\text{-}$$

in which Rf1 is a linear, cyclic or branched, partially or fully fluorinated aliphatic group of 1 to 10 carbon atoms, Rf2 and Rf3 each independently represent a linear perfluorinated alkylene of 1, 2, 3 or 4 carbon atoms and p and q each independently represent 1, 2, 3 or 4, wherein the total number of carbon atoms in Rf1' is equal to or less than 10;

Rf2' corresponds to the general formula $$\text{Rf4-O—}(CF_2)_b\text{—}$$

in which Rf4 is a linear, cyclic or branched, partially or fully fluorinated alkylene having 1, 2, 3 or 4 carbon atoms, preferably and b represents 1, 2, 3, 4, 5 or 6 and wherein the total number of carbon atoms in Rf2' is equal to or less than 10;

Rf3' corresponds to the general formula $$\text{Rf5-}(CF_2)_c\text{—}$$

in which Rf5 is a linear, cyclic or branched, partially or fully fluorinated alkylene having 1, 2, 3 or 4 or up to 9 carbon atoms, preferably and c represents 1, 2, 3, 4, 5 or 6 and wherein the total number of carbon atoms in Rf3' is equal to or less than 10;

Rf4' corresponds to the general formula $$\text{Rf6-O—}(CF_2)_d\text{—O—}(CF_2)_e\text{—}$$

in which Rf6 is a linear, cyclic or branched, partially or fully fluorinated alkylene having 1, 2, 3 or 4 carbon atoms, preferably and b and c each independently represent 1, 2, 3 or 4 and wherein the total number of carbon atoms in R42' is equal to or less than 10.

4. The method according to claim 1 wherein Rf is linear.

5. The method according to claim 1 wherein the reaction medium comprises an equal or greater amount (in volume) of organic solvent than water.

* * * * *